US008679805B2

(12) United States Patent
Chung et al.

(10) Patent No.: US 8,679,805 B2
(45) Date of Patent: Mar. 25, 2014

(54) PREPARATION METHOD OF TRANSPORTATION FUEL OR LUBRICATING BASE OIL USING BIOMASS

(75) Inventors: Young Min Chung, Daejeon (KR); Ok Youn Kim, Daejeon (KR); Hee Jung Jeon, Daejeon (KR); Young Seek Yoon, Gwangju (KR); Seong Ho Lee, Seoul (KR); Hee Soo Kim, Daejeon (KR); Seung Hoon Oh, Seoul (KR); Yoon Jae Yim, Chungcheongnam-do (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 13/635,584

(22) PCT Filed: Mar. 14, 2011

(86) PCT No.: PCT/KR2011/001754
§ 371 (c)(1),
(2), (4) Date: Sep. 17, 2012

(87) PCT Pub. No.: WO2011/115394
PCT Pub. Date: Sep. 22, 2011

(65) Prior Publication Data
US 2013/0017590 A1    Jan. 17, 2013

(30) Foreign Application Priority Data

Mar. 19, 2010  (KR) .................. 10-2010-0024794
Jul. 20, 2010   (KR) .................. 10-2010-0069983

(51) Int. Cl.
*C12P 5/02* (2006.01)
(52) U.S. Cl.
USPC ........................................................ 435/167
(58) Field of Classification Search
USPC ........................................................ 435/167
See application file for complete search history.

(56) References Cited

U.S. PATENT DOCUMENTS

| | | | |
|---|---|---|---|
| 5,874,263 A | 2/1999 | Holtzapple et al. | |
| 5,969,189 A | 10/1999 | Holtzapple et al. | |
| 6,043,392 A | 3/2000 | Holtzapple et al. | |
| 7,351,559 B2 | 4/2008 | Verser et al. | |
| 2007/0135316 A1* | 6/2007 | Koivusalmi et al. | 508/216 |
| 2007/0161832 A1* | 7/2007 | Myllyoja et al. | 585/7 |
| 2007/0244343 A1 | 10/2007 | Brevoord et al. | |
| 2008/0280338 A1 | 11/2008 | Hall et al. | |
| 2009/0239279 A1 | 9/2009 | Hall et al. | |

FOREIGN PATENT DOCUMENTS

| | | |
|---|---|---|
| KR | 10-2008-0079310 A | 8/2008 |
| WO | 2007-068795 A1 | 6/2007 |
| WO | 2007-068800 A2 | 6/2007 |
| WO | 2008-152200 A | 12/2008 |

OTHER PUBLICATIONS

Osamu Nagashima, et al., "Ketonization of carboxylic acids over CeO2-based composite oxides," Journal of Molecular Catalysis, 227:231-239 (2005).
Edward L. Kunkes, et al., "Catalytic Conversion of Biomass to Monofunctional Hydrocarbons and Targeted Liquid-Fuel Classes," Science, 322:417-421 (Oct. 17, 2008) (including "Suppoerting Online Material").
International Search Report for PCT/KR2011/001754, Nov. 24, 2011 (6 pages).

* cited by examiner

*Primary Examiner* — Ralph Gitomer
(74) *Attorney, Agent, or Firm* — Abelman, Frayne & Schwab

(57) ABSTRACT

The present invention relates to a method of economically preparing paraffin compounds corresponding to gasoline fuel or lubricating base oil using volatile fatty acids (VFAs) derived from biomass.

17 Claims, 1 Drawing Sheet

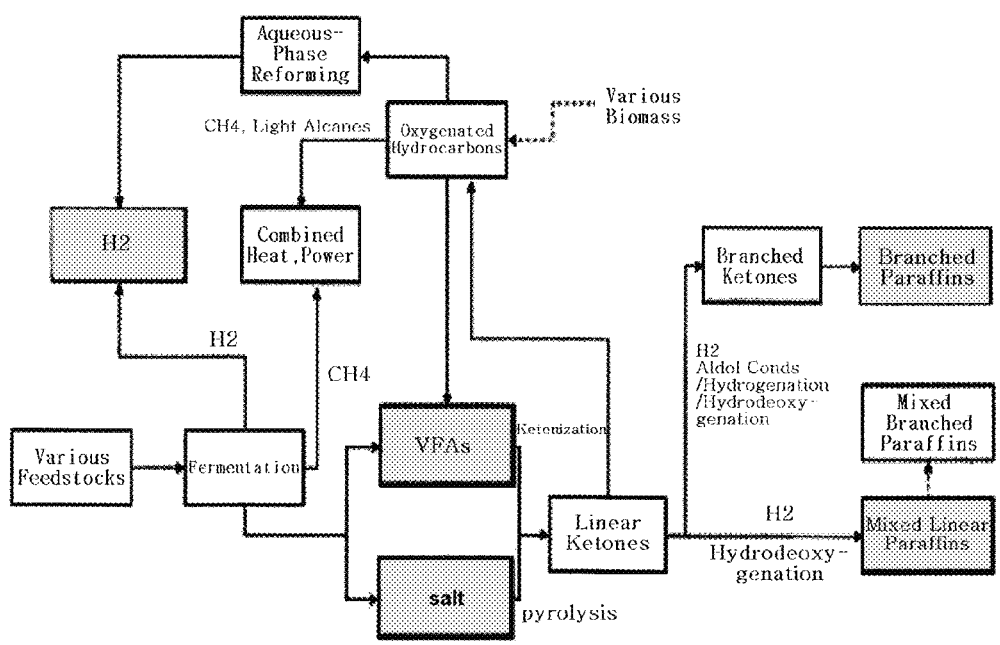

PREPARATION METHOD OF TRANSPORTATION FUEL OR LUBRICATING BASE OIL USING BIOMASS

RELATED APPLICATIONS

This application is a United States national phase application under 35 USC §371 of PCT/KR2011/001754 filed on Mar. 14, 2011, and claims the benefit under 35 USC §119 of Korean patent application numbers KR 10-2010-0024794 filed Mar. 19, 2010 and KR 10-2010-0069983 filed Jul. 20, 2010, the disclosures of which are all incorporated herein by reference in their entireties.

TECHNICAL FIELD

The present invention relates to a method of economically preparing paraffinic compounds corresponding to gasoline fuel or lubricating base oil using volatile fatty acids (VFAs) derived from biomass. More specifically, the present invention relates to a method of preparing a branched non-polar paraffinic transportation fuel or lubricating base oil in high yield by converting volatile fatty acids, obtained by fermentation of raw materials from biological sources, into a mixture of ketones by a catalytic reaction, and subjecting the ketone mixture to aldol condensation, hydrogenation and hydrodeoxygenation alone or sequentially.

BACKGROUND ART

Fossil fuels or petroleum-based fuels have formed the basis for energy production and transportation. In recent years, due to rising costs and threats of shortages and supply interruptions, biofuels have particularly received as alternative fuels to petroleum-based products.

Biofuel is generally regarded as any fuel derived from biomass. The term biomass is often used in regard to plant-based sources, such as corn, soy beans, flaxseed, sugar cane, and palm oil, but the term can generally extend to any recently living organisms, or their metabolic byproducts, that play a part in the carbon cycle.

The studies done into the production of bioenergy from biomass have mainly been into alternative fuels that can replace transportation oil-based fuel (gasoline and diesel). As an alternative to gasoline, bioethanol which is prepared by fermentation of sugar cane, corn or the like was developed and commercialized. Likewise, as an alternative to diesel, biodiesel, such as FAME, HBD or the like, which is prepared by treating plant-based oil such as palm oil, soybean oil or the like, was developed and commercialized.

However, in the prior art, there has been an ethical problem in that edible plants such as plants and plant oils are used as the raw materials to prepare bioethanol and biodiesel. In addition, supplying the raw materials is not easy, and the economy is being reduced rapidly due to a rapid increase in the cost of the raw materials. In an attempt to solve these problems, studies on the use of non-edible plants as raw materials have been actively conducted, but a clear solution has not yet been found.

Among recent studies on the preparation of transportation fuels from biomass is a study which has been receiving attention that is a method comprising obtaining C6 sugar/polyol from woody biomass through various pretreatment steps, preparing a mixture of alcohol, organic acid, cyclic furan and the like from the C6 sugar/polyol using a Pt—Re/C catalyst, and preparing oil fractions such as gasoline, aromatics and diesel from the mixture by various chemical reaction pathways [Science 322 (2008) 417]. However, due to low yield, high pretreatment cost, the use of a large amount of hydrogen, complicated reaction pathways, and the like, this method will require a long time until it is applied to actual commercial processes.

Volatile fatty acids (VFAs) can be obtained in high yield from various raw materials, including woody biomass, seaweeds and organic waste, by simple fermentation, and studies on the preparation of transportation oil from such volatile fatty acids are in progress. Generally, there is a known method for preparing mixed alcohols from the mixed fatty acids or mixed ketones obtained by fermentation. Furthermore, a method is known which comprises preparing mixed olefins by the dehydration of alcohols and oligomerizing the olefins to prepare gasoline and diesel fractions.

U.S. Pat. No. 5,874,263 discloses that volatile fatty acids or their metal salts can be prepared by anaerobic fermentation of biomass. Specifically, the productivity of volatile fatty acids and their calcium salts, which are obtained by fermentation, can be increased by pretreating biomass with slaked lime under anaerobic conditions and increasing the initial volatile fatty acid levels.

Methods of preparing volatile fatty acids or ketone mixtures using metal salts of volatile fatty acids produced by fermentation are as follows. U.S. Pat. No. 5,969,189 discloses methods of forming calcium carbonate by pyrolysis of calcium salts of volatile fatty acids prepared as described above, and preparing ketone mixtures from volatile fatty acids. U.S. Pat. No. 6,043,392 discloses a method comprising substituting metal salts of volatile fatty acids, prepared by anaerobic fermentation, with an amine to prepare amine carboxylates, and pyrolyzing the amine carboxylates, thereby preparing volatile fatty acids and preparing aldehyde, alcohol and lactic acid as byproducts.

Methods of preparing transportation fuels directly from the volatile fatty acids prepared by the above-described methods are as follows. U.S. Pat. No. 7,351,559 discloses a method of preparing ethanol usable as fuel by fermenting biomass to prepare acetic acid and acetate, which are then esterified to ethyl acetate, followed by hydrogenation. US 20080280338 discloses a method of preparing liquid fuel usable as transportation fuel by preparing acetylene from the alcohol and methane derived from volatile fatty acids, and converting the acetylene to ethylene, followed by oligomerization. US 20090239279 discloses a method for increasing the efficiency of preparation of liquid fuel by mixing a hydrocarbon and a pyrolysis oil obtained by biomass other than the above alcohol and methane and oligomerizing the mixture.

However, in the processes of obtaining branched fuels by oligomerization, there are shortcomings in that the catalyst is rapidly inactivated due to the production of coke, and thus a fluidized bed reactor having high equipment and operating costs should be used.

Furthermore, conventional biofuels such as bioethanol and biodiesel could substitute for only a portion of petroleum-based gasoline and diesel, because the physical properties thereof differ from those of these petroleum-based fuels. However, if transportation fuel or lubricating base oil prepared from biological sources has quality equal to or higher than that of conventional petroleum-based transportation fuel or lubricating base oil and can substitute for all of the conventional petroleum-based fuels, the technical value thereof appears to be higher.

In addition, there is a need for studies into methods capable of preparing branched non-polar paraffinic transportation fuel or lubricating base oil in high yield by carrying a catalytic reaction of volatile fatty acids from natural sources and subjecting the catalytic reaction products to aldol condensation, hydrogenation and hydrodeoxygenation alone or sequentially.

DISCLOSURE

Technical Problem

Accordingly, the present inventors have conducted studies to overcome the above-described problems occurring in the prior art and have recognized that, if an alternative method of preparing volatile fatty acids from biological waste, which has a low resource value and causes environmental pollution, and efficiently preparing transportation fuel or lubricating base oil from the volatile fatty acid, is developed, it can maximize economic efficiency and contribute to environmental improvement, thereby culminating in the present invention as described below.

Therefore, it is an object of the present invention to provide a method of preparing hydrocarbons, which can be used as transportation fuel and lubricating base oil, from materials of biological sources. More specifically, an object of the present invention is to provide a method of preparing a branched non-polar paraffinic transportation fuel or lubricating base oil in high yield by carrying out of volatile fatty acids, obtained by fermentation of raw materials from biological sources, and subjecting the catalytic reaction products to aldol condensation, hydrogenation and hydrodeoxygenation alone or sequentially.

An object of the present invention is not limited to the above-mentioned object, and other objects of the present invention will be clearly understood by one skilled in the art from the following description.

Technical Solution

In order to overcome the above-described problems, the present invention proposes a method of preparing a branched non-polar paraffinic transportation fuel or lubricating base oil by converting volatile fatty acids, obtained by fermentation of raw materials from biological sources, into a mixture of ketones by a catalytic reaction, and subjecting the ketone mixture to aldol condensation and hydrodeoxygenation alone or sequentially in the presence of a catalyst.

To the above object, the present invention provides a method for preparing transportation fuel or lubricating base oil, the method comprising the steps of:

A) preparing C2-C7 volatile fatty acids or their salts by fermentation of biomass;

B) producing a mixture of C3-C13 ketones from the volatile fatty acids or their salts of step A); and C) converting the ketone mixture of step B) into paraffins corresponding to transportation fuel or lubricating base oil in the presence of a hydrogenation catalyst.

According to one embodiment of the present invention, in order to prepare transportation fuel or lubricating base oil, step C) comprises the steps of:

i) subjecting the ketone mixture to aldol condensation to prepare hydroxyketones having an increased carbon chain length;

ii) dehydrating the hydroxyketones to form enones;

iii) saturating the enones with hydrogen to form ketones; and iv) converting the formed ketones into branched non-polar paraffins by hydrodeoxygenation.

According to one embodiment of the present invention, the method may further comprise, between steps ii) and iii), the steps of:

iii-a) reacting the enones with a ketone to form hyroxyenones having an increased carbon chain length; and iii-b) dehydrating the hyroxyenones.

According to one embodiment of the present invention, the method may further comprise, between steps ii) and iii), the steps of:

iii-c) saturating the enones with hydrogen;

iii-d) subjecting the ketone mixture to aldol condensation to prepare hydroxyketones having an increased cathon chain length;

iii-e) dehydrating the hydroxyketones to form enones having an increased cathon chain length; and iii-f) saturating the enones of step iii-e) with hydrogen.

According to one embodiment of the present invention, the method may further comprise, after step C), step D) of subjecting the produced paraffin to skeletal isomerization.

Advantageous Effects

According to the present invention, a mixture of ketones can be produced from volatile fatty acids derived from a variety of biomass, and from the ketone mixture, branched non-polar paraffinic compounds which can be used as transportation or lubricating base oil can then be prepared. Thus, it is possible to obtain transportation oil or lubricating base oil from entirely new sources that are not based on petroleum.

Unlike the prior art, because a variety of biomass can be used as the raw material, the present invention has advantages in that the raw materials can be guaranteed to be present in large amounts and economic efficiency can be significantly increased.

The branched non-polar paraffinic compounds prepared according to the present invention can be used as high-quality fuels having high oxidation stability and high stability at low temperature, because they are free of deactivation materials, including sulfur, nitrogen and aromatic compounds, and are based on paraffin. Unlike conventional bio-oils, the paraffinic compounds of the present invention can be used as transportation fuel or lubricating base oil without limitation on blending.

Particularly, in the process of preparing lubricating base oil, an isomerization reaction is generally carried out in order to increase the low-temperature stability of the lubricating base oil, but in the reaction of preparing lubricating base oil according to the present invention, an isomerization reaction does not need to be applied.

In addition, when using a catalyst system prepared either by physically mixing materials having one or more of the condensation, hydrogenation and hydrodeoxygenation functions disclosed in the present invention, or by shaping the materials using a binder, or by forming a double-bed catalyst system using the materials, paraffins can be prepared in high yield by subjecting a mixture of ketones, obtained by various methods, to aldol condensation, hydrogenation and hydrodeoxygenation alone or sequentially.

DESCRIPTION OF DRAWINGS

FIG. 1 is a schematic view showing an overall reaction pathway according to an embodiment of the present invention.

BEST MODE

Hereinafter, the technical idea of the present invention will be described in further detail with reference to the accompanying drawings.

As described above, the method for preparing transportation fuel or lubricating base oil according to the present invention comprises the steps of: preparing C2-C7 volatile fatty acids by fermentation of biomass; subjecting the volatile fatty acids to ketonization to produce a mixture of C3-C13 ketones; and converting the produced ketones into paraffins in the presence of a hydrogenation catalyst. In one embodiment, the step of converting the ketones into the paraffins may be carried out by hydrodeoxygenation. The paraffins produced directly from the ketone mixture by hydrodehydrogenation may be C3-C13 linear paraffins. The linear paraffins can be converted to branched paraffins by an isomerization reaction.

In another embodiment, the step of converting the ketones to the paraffins may comprise the steps of: converting the produced ketones to ketones having an increased carbon chain length by aldol condensation; and converting the converted ketones to paraffins by hydrodeoxygenation. The paraffins produced according to this embodiment may be C6-C60 branched paraffins. The step of converting the ketones to the paraffins may be carried out in a single catalyst system or a single reactor, and the aldol condensation and hydrodeoxygenation reactions may be carried out by separate continuous processes.

Hereinafter, the above embodiment will be described in further detail.

In the present invention, C2-C4 volatile fatty acids and a mixture thereof, produced by fermentation of biomass, are used as raw materials. In addition, synthetic materials corresponding thereto may also be used as raw materials.

FIG. 1 is a schematic view showing an overall reaction pathway according to the present invention. As can be seen in FIG. 1, the present invention relates to a method of preparing paraffinic compounds, particularly branched paraffinic compounds, which correspond to gasoline fuel or lubricating base oil, using volatile fatty acids (VFAs) derived from biomass. Producing aldehydes, ketones and alcohols from fats from biological sources and subjecting the products to aldol condensation can be contemplated. However, when aldehydes, ketones and alcohols derived from non-volatile fats that are not volatile fatty acids are used as raw materials, there will be problems, namely the supply of the raw materials is limited and an isomerization step should necessarily be carried out in order to prepare lubricating base oil, because the hydrocarbon length of the raw materials is long. In addition, because fats having a high olefin content are used as raw materials, undesired naphthenic compounds will also be produced due to the influence of olefins in the aldol condensation step. Furthermore, because the reaction phases of aldol condensation and hydrodeoxygenation differ from each other, it will be impossible to prepare lubricating base oil by carrying out sequential reactions in a single step or in a single reactor.

Volatile fatty acids derived from biomass can be produced by fermentation of conventional biomass materials. Volatile fatty acids (VFAs) which are used in the present invention are C2-C7 water soluble carboxylic acids or mixtures thereof and have, for example, the following structure:

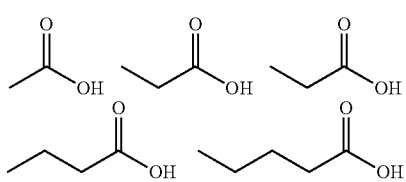

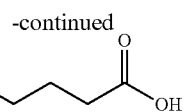

In the embodiment of the present invention, the fatty acids are converted into a mixture of C3-C7 ketones by ketonization. Meanwhile, the ketone mixture may also be obtained directly by pyrolysis of volatile fatty acid salts produced in the fermentation process. The ketonization reaction is shown in, for example, the following reaction scheme 1:

[Reaction Scheme 1]

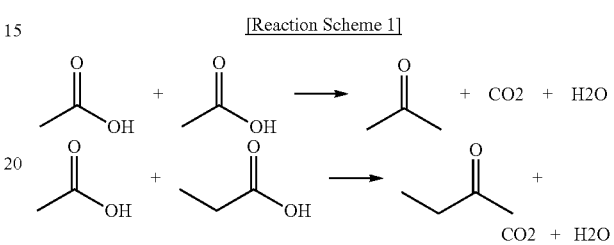

The conversion of the carboxylic acids to the ketones may be carried out using a process known in the art. For example, a catalyst which is used for this conversion may include either titania or a zirconium dioxide or Cerium dioxide supported on alumina. The temperature in the reaction zone may be in the range of 200 to 600° C. The ketonization reaction may be carried out under a wide range of pressure, preferably 1-200 psi. The mixed ketones prepared by the above method have the following structures:

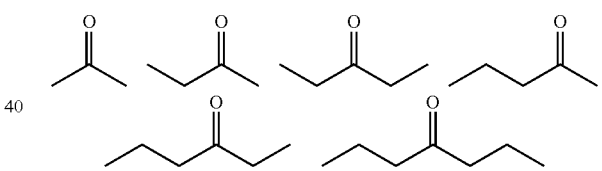

The produced ketone mixture is linear and may be subjected to aldol condensation to form a ketone having a larger carbon number. If the aldol condensation is not carried out, the mixture of linear ketones may be subjected to hydrodeoxygenation to produce linear paraffins. The aldol condensation is carried out according to, for example, the following reaction scheme 2:

[Reaction Scheme 2]

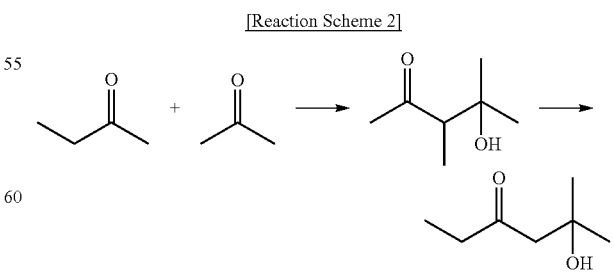

The aldol condensation according to the present invention is preferably carried out in a hydrogen atmosphere. In this case, the equilibrium reaction can be shifted from the produced enones to branched ketones as described below, and thus the rate of the aldol condensation reaction that is the rate determining step can be increased.

The hydrogenated ketones resulting from the condensation reaction as described above is dehydrated to remove the water molecule while producing a double bond. Thus, the dehydration reaction results in enone compounds. This dehydration reaction pathway is, for example, as follows:

[Reaction Scheme 3]

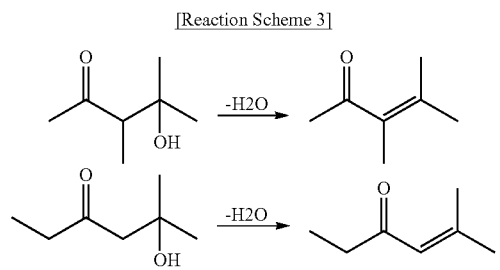

The double bond in the enone compounds can be hydrogenated at low temperature, and thus the enone compounds can be converted to branched ketone compounds as follows:

[Reaction Scheme 4]

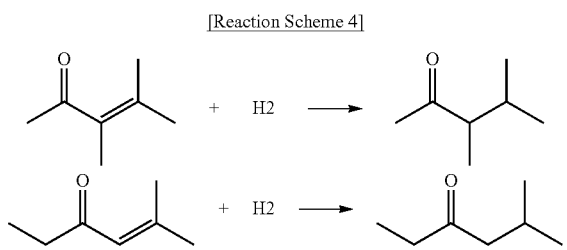

The branched ketone compounds as described above can be converted to branched paraffinic compounds by hydrodeoxygenation as follows:

[Reaction Scheme 5]

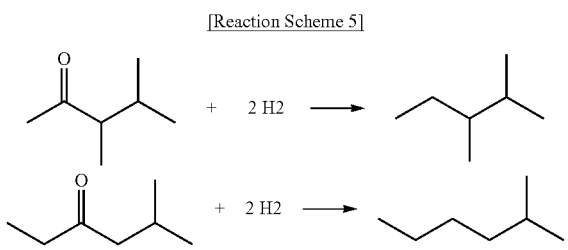

As a result, according to the above reaction schemes 2 to 5, C3-C60 linear or branched paraffins can be selectively prepared from the mixture of C3-C13 ketones, and among the prepared paraffins, C6-C14 branched non-polar paraffins can be used directly as transportation fuel without limitation on blending.

If the hydrodeoxygenation reaction occurs on linear ketone compounds, linear paraffins are mainly produced. The linear paraffins can be converted to branched paraffins by isomerization. The isomerization reaction is carried out under the conditions known in the art.

In the method according to the present invention, the pathway used to prepare branched transportation fuel from the mixture of linear ketones can be summarized as follows:

[Reaction Scheme 6]

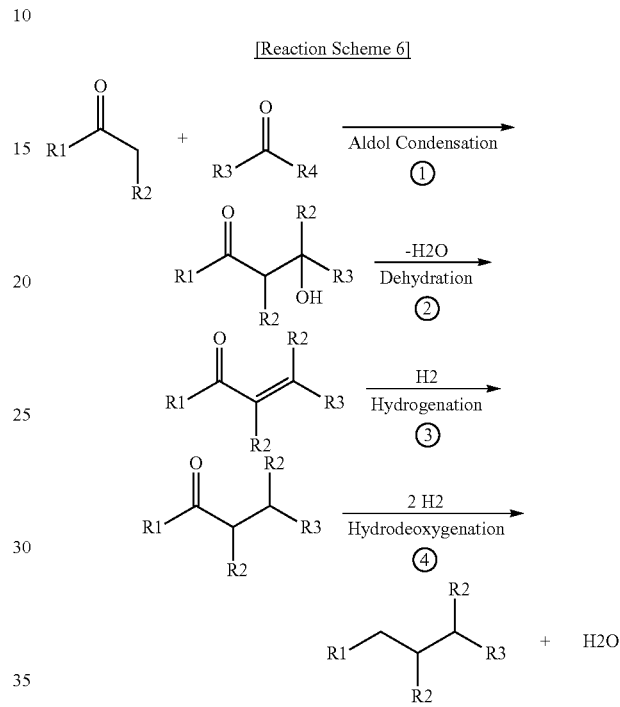

In one embodiment of the present, the method for preparing transportation fuel or lubricating base oil comprises the steps of:

i) subjecting a mixture of ketones to aldol condensation to prepare hydroxyketones having an increased carbon chain length;

ii) dehydrating the hydroxyketones to form enones;

iii) saturating the enones with hydrogen to form ketones; and iv) converting the produced ketones of step to branched non-polar paraffins by hydrodeoxygenation.

In the present invention, it was confirmed that reactions ① to ④ in reaction scheme 6 can be carried out in separate reactors or two or more reactors, but are preferably carried out in one reactor. The enones produced by reaction ② are unstable and thus easily ketonized at low temperature. As a result, the rate of reaction ③ is higher than those of other reactions. If reaction ③ proceeds fast and the concentration of the enones decrease, reaction ② is accelerated and, for the same reason, aldol condensation ① (equilibrium reaction) is accelerated. Because reaction ④ easily proceeds under the reaction conditions, the conversion rate is higher in the case in which the aldol condensation reaction and the hydrodeoxygenation reaction are carried out in one step in one reactor than in the case in which these reactions are carried out separately.

In addition, when using a catalyst system prepared either by physically mixing materials having one or more of the condensation, hydrogenation and hydrodeoxygenation functions, or by shaping the materials using a binder, or by forming a double-bed catalyst system using the materials, the yield of the branched non-polar paraffins can be significantly increased.

A catalyst having a condensation function may be any material having an acid or base functionality. Examples thereof include CeZrOx, CuZrOx, hydrotalcite, niobium oxide, alumina, silica, silica-alumina, zirconia, titania, or mixed oxides thereof, or molecular sieves, including zeolite.

As a catalyst useful for hydrogenation, any metal material having a hydrogenation function may be used. Specifically, it may include a metal component selected from among group VIII metals, group VI metals, and mixtures thereof. Preferably, the metal component may be selected from the group consisting of Pd, Pt, Rh, Ru, Ni, Cu, V, Fe, Co, Mo, W, NiMo, CoMo, NiW, and CoW.

A catalyst having a hydrodeoxygenation function is preferably a catalyst having both a hydrogenation function and a deoxygenation function and can be prepared by loading the metal component having a hydrogenation function on the material having an acid or bass functionality.

Meanwhile, steps i) to v) may be carried out in a single catalyst system or rector at a temperature of 80 to 500° C. at a hydrogen pressure of 1-200 bar. Preferably, these steps may be carried out at a temperature of 100 to 400° C. at a pressure of 5-50 bar in a hydrogen atmosphere. WHSV in the single reactor is 0 to 5/hr, preferably 0 to 2/hr, more preferably 0 to 1/hr, and most preferably more than 0 to 0.6/hr.

Under conditions deviating from the above-described conditions, the reaction can be incomplete. For example, under the conditions of lower temperature, lower pressure and shorter residence time than the above-described conditions, the conversion rate can decrease, and under the conditions of higher temperature, higher pressure and longer residence time than the above-described conditions, high-boiling-point hydrocarbons can significantly increase.

The reaction of preparing lubricating base oil is carried out according to the same principle as the above-described reaction, but is carried out by a reaction in which the carbon chain length becomes longer by aldol condensation. The increase in the carbon chain length by aldol condensation can be achieved by two methods as follows.

In one method, the ketones derived from volatile fatty acids are additionally subjected to aldol condensation in an enone state having a carbon chain length which was increased by aldol concentration.

Specifically, the method for preparing transportation fuel or lubricating base oil according to one embodiment of the present invention comprises the steps of:
  i) subjecting a mixture of ketones to aldol condensation to prepare hydroxyketones having an increased cathon chain length;
  ii) dehydrating the hydroxyketones to form enones;
  iii-1) reacting the enones with a ketone to form hydroxyenones having an increased cathon chain length;
  iv) dehydrating and hydrogenating the hydroxyenones to form ketones having an increased cathon chain length; and
  v) converting the produced ketones to branched non-polar paraffins by hydrodeoxygenation.

According to another embodiment of the present invention, the method for preparing transportation fuel or lubricating base oil comprises the steps of:
  i) subjecting a mixture of ketones to aldol condensation to prepare hydroxyketones having an increased cathon chain length;
  ii) dehydrating the hydroxyketones to form enones;
  iii-a) reacting the enones with a ketone to form hydroxyenones having an increased carbon chain length;
  iii-b) dehydrating the hydroxyenones;
  iv) hydrogenating the dehydrated enones to form ketones having an increased cathon chain length; and
  v) converting the formed ketones to branched non-polar paraffins by hydrodeoxygenation.

In another method, stabilized ketones (enones) are additionally subjected to aldol condensation with a ketone derived from volatile fatty acid.

Specifically, the method for preparing transportation fuel or lubricating base oil according to one embodiment of the present invention comprises the steps of:
  i) subjecting a mixture of ketones to aldol condensation to prepare hydroxyketones having an increased cathon chain length;
  ii) dehydrating the hydroxyketones to form enones;
  iii) hydrogenating the enones to form ketones, followed by aldol condensation to increase the carbon chain length of the ketones;
  iv) dehydrating and hydrogenating the ketones; and
  v) converting the ketones to branched non-polar paraffins by hydrodeoxygenation.

According to another embodiment of the present invention, the method for preparing transportation fuel or lubricating base oil comprises the steps of:
  i) subjecting a mixture of ketones to aldol condensation to prepare hydroxyketones;
  ii) dehydrating the hydroxyketones to form enones;
  iii-c) saturating the enones with hydrogen to form ketones;
  iii-d) subjecting the ketones of step iii-c) to aldol condensation to form hydroxyketones having an increased cathon chain length;
  iii-e) dehydrating the ketones to form enones having an increased cathon chain length;
  iv) hydrogenating the enones of step iii-e) to form ketones having an increased cathon chain length; and
  v) converting the ketones of step iv) to branched non-polar paraffins by hydrodeoxygenation.

Step i) to v) according to the above embodiment can be explained by the following reaction scheme 7. Steps i) to v) as shown in reaction scheme 7 can be carried out simultaneously in a catalyst system or reactor or divided into an aldol condensation reaction and a hydrodeoxygenation reaction and can be sequentially carried out using their own catalysts and reactors.

[Reaction Scheme 7]

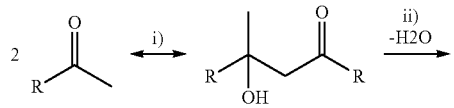

-continued

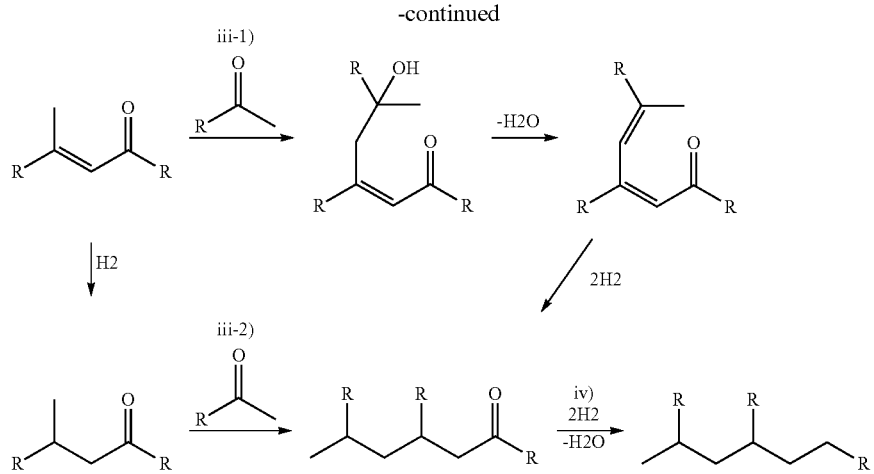

When steps i) to v) are carried out simultaneously using a single catalyst in a single reactor, the hydrogenation catalyst may be the same as described above. In other words, the catalyst may comprise a metal component selected from among group VIII metals, group VI metals, and mixtures thereof. Preferably the metal component may be Pd, Pt, Rh, Ru, Ni, Cu, V, Fe, Co, Mo, W, or a mixture of two or more thereof particularly NiMo, CoMo, NiW, or CoW. Furthermore, the catalyst may further comprise a support which may be CuZrOx, hydrotalcite, niobium oxide, alumina, silica, carbon, silica-alumina, zirconia or titanic.

Meanwhile, steps i) to v) may be carried out in a single catalyst system or reactor at a temperature of 80 to 500° C. at a hydrogen pressure of 1-200 bar. Preferably, these steps may be carried out at a temperature of 100 to 400° C. at a pressure of 5-50 bar in a hydrogen atmosphere. In addition, WHSV in the single reactor is 0 to 5/hr, preferably 0 to 2/hr, more preferably 0 to 1/hr, and most preferably 0 to 0.6/hr.

Under conditions deviating from the above-described conditions, the reaction may be incomplete. For example, under the conditions of lower temperature, lower pressure and residence time shorter than the above-described conditions, the conversion rate can decrease, and under the conditions of higher temperature, higher pressure and longer residence time than the above-described conditions, high-boiling-point hydrocarbons can significantly increase.

As described above, the carbon chain length can be increased to form C6-C60 ketones which can be hydrodeoxygenated to prepare C6-C60 branched paraffins which are used as transportation fuel or lubricating base oil.

The lubricating base oil prepared as described above can correspond to Group III lubricating base oil and does not require additional isomerization, unlike general petroleum-based lubricating base oils. In addition, because it is prepared by aldol polycondensation from volatile fatty acids that are not non-volatile fats, it is a pure, branched non-polar paraffinic lubricating base oil containing no naphthenic structure. Particularly, the branched non-polar paraffinic lubricating base oil is a high-quality lubricating base oil containing no deactivation materials and having very excellent low-temperature stability and oxidation stability. In addition, it is compatible with existing lubricating oil additives.

In the present invention, in the hydrogenation reaction following the production of linear ketone compounds, only 3 moles of hydrogen are required to prepare branched paraffinic transportation from 2 mole of volatile fatty acid, and thus the consumption of hydrogen is very low compared to the prior art. Additionally, because hydrogen produced in the process of fermenting biomass can be used, the method of the present invention is relatively advantageous in terms of the supply of H2 and is highly economical.

MODE FOR INVENTION

Hereinafter, the present invention will be described in further detail with reference to examples. It is to be understood, however, that the scope of the present invention is not limited to these examples and the present invention can be embodied in various ways within the scope of the present invention.

Example 1

A mixture of ketones was prepared from volatile fatty acids, derived from biomass, using a known technique [Journal of Molecular Catalysis A: Chemical 227 (2005) 231-239]. The composition of this ketone mixture is shown in Table 1 below. For the ketone mixture having the composition shown in Table 1, an experiment of preparing branched paraffinic hydrocarbons was carried out using a 0.2 wt % Pd/Nb$_2$O$_5$ catalyst. The 0.2 wt % Pd/Nb$_2$O$_5$ catalyst was prepared by loading Pd(NO$_3$)$_2$ (10 wt % Aldrich) onto niobic acid by an incipient wetness method, drying the loaded material at 393 K for 3 hours, and calcining the dried material at 533 K for 3 hours in an air atmosphere. The reaction was carried out using a high-pressure micro-reactor, and 6 g of the 0.2 wt % Pd/Nb$_2$O$_5$ catalyst prepared by the above was used in the experiment. The reduction of the catalyst was performed by heating it to 723 K at a rate of 0.5° C./min at a hydrogen flow rate of 200 sccm, maintaining it at that temperature for 2 hours and reducing the temperature to 623 K. At a temperature of 623 K, the ketone mixture was introduced by an upflow method at a WHSV of 0.5 h$^{-1}$ while the pressure of hydrogen was adjusted to 50 bar and the ratio of hydrogen/raw material introduced was adjusted to 5. After the reaction, the conversion of each of the mixed ketones was analyzed by GC, and the results of the analysis are shown in Table 2 below.

TABLE 1

| Number of carbon atoms | Name | Content (wt %) |
| --- | --- | --- |
| C3 | Dimethyl ketone (DMK) | 60 |
| C4 | Methyl ethyl ketone (MEK) | 20 |
| C5 | Methyl propyl ketone (MPK) | 10 |
| C5 | Diethyl ketone (DEK) | 5 |
| C6 | Ethyl propyl ketone (EPK) | 3 |
| C7 | Dipropyl ketone (DPK) | 2 |

TABLE 2

| Ketones | Conversion (%) |
| --- | --- |
| Dimethyl ketone (DMK) | 95 |
| Methyl ethyl ketone (MEK) | 90 |
| Methyl propyl ketone (MPK) | 88 |
| Diethyl ketone (DEK) | 73 |
| Ethyl propyl ketone (EPK) | 85 |
| Dipropyl ketone (DPK) | 99 |

The product was analyzed by GC-MS, Simdist and the like, and the composition of the product is shown in Table 3 below.

TABLE 3

| Product | Selectivity (%) |
| --- | --- |
| Linear paraffins (<C5) | 4 |
| Branched paraffins (C6-C20) | 42 |
| Branched ketones (C6-C14) | 25 |
| Branched olefins (C4-C16) | 19 |
| Alcohols (C4-C10) | 6 |
| Aromatics (C7-C8) | 4 |

Example 2

For the ketone mixture having the composition shown in Table 1, an experiment of preparing branched paraffinic hydrocarbons was carried out using a Cu/Mg$_{10}$Al$_7$Ox catalyst. The Cu/Mg$_{10}$Al$_7$Ox catalyst was prepared by mixing Cu, Mg and Al nitrate precursors at a molar ratio of 1:10:7 and co-precipitating the mixture at pH of 10 using a mixed solution of KOH and K$_2$CO$_3$. The prepared cake was stirred at 338 K while distilled water was added dropwise thereto, and then allowed to stand for 2 hours, and the precipitate was filtered and washed. The washed material was dried at 393 K for a sufficient time and calcined at 773 K in an air atmosphere for a sufficient time. For the reduction of the catalyst, 6 g of the catalyst was introduced in a high-pressure micro-reactor in which it was reduced in-situ at 573 K at a hydrogen flow rate of 200 sccm for 1 hour. The reaction for preparing branched paraffinic compounds was carried out under the same conditions as Example 1. After the reaction, the conversion of each of the mixed ketones was analyzed by GC, and the results of the analysis are shown in Table 4 below.

TABLE 4

| Ketones | Conversion (%) |
| --- | --- |
| Dimethyl ketone (DMK) | 88 |
| Methyl ethyl ketone (MEK) | 90 |
| Methyl propyl ketone (MPK) | 85 |
| Diethyl ketone (DEK) | 78 |
| Ethyl propyl ketone (EPK) | 82 |
| Dipropyl ketone (DPK) | 57 |

The product was analyzed in the same manner as Example 1, and the results of the analysis are shown in Table 5 below.

TABLE 5

| Product | Selectivity (%) |
| --- | --- |
| Linear paraffins (<C5) | 2 |
| Branched paraffins (C6-C20) | 33 |
| Branched ketones (C6-C14) | 35 |
| Branched olefins (C4-C16) | 25 |
| Alcohols (C4-C10) | 4 |
| Aromatics (C7-C8) | 1 |

Example 3

For the ketone mixture having the composition shown in Table 1, an experiment of preparing branched paraffins was carried out using a 0.2 wt % Pd/CeZrOx catalyst. To prepare the 0.2 wt % Pd/CeZrOx catalyst, the CeZrOx support was prepared in the following manner. Ce(No$_3$)$_3$6H$_2$O and ZrO(NO$_3$)$_2$ were mixed at a ratio of 1:1 and co-precipitated for 65 hours while the pH was kept of 10 with NH$_4$OH. The precipitate was filtered, washed, dried at 383 K for a sufficient time and then calcined at 723 K for 2 hours. To reduce the catalyst, 6 g of the catalyst was introduced in a high-pressure micro-reactor in which it was reduced by heating it to 623 K at a rate of 0.5° C./min and maintaining it at a hydrogen flow rate of 200 sccm for 2 hours. The reaction for preparing branched paraffinic compounds was carried out under the same conditions as Example 1. After the reaction, the conversion of each of the mixed ketones was analyzed by GC, and the results of the analysis are shown in Table 6 below.

TABLE 6

| Ketones | Conversion (%) |
| --- | --- |
| Dimethyl ketone (DMK) | 100 |
| Methyl ethyl ketone (MEK) | 95 |
| Methyl propyl ketone (MPK) | 92 |
| Diethyl ketone (DEK) | 72 |
| Ethyl propyl ketone (EPK) | 83 |
| Dipropyl ketone (DPK) | 75 |

The product was analyzed in the same manner as Example 1, and the results of the analysis are shown in Table 7 below.

TABLE 7

| Product | Selectivity (%) |
| --- | --- |
| Linear paraffins (<C5) | 1 |
| Branched paraffins (C6-C20) | 25 |
| Branched ketones (C6-C14) | 47 |
| Branched olefins (C4-C16) | 26 |
| Alcohols (C4-C10) | Trace |
| Aromatics (C7-C8) | 1 |

Example 4

A mixture of ketones was prepared from volatile fatty acids, derived from biomass, using a known method [Journal of Molecular Catalysis A: Chemical 227 (2005) 231-29], and the composition of the ketone mixture is shown in Table 1. For the ketone mixture having the composition shown in Table 1, an experiment of preparing branched paraffinic hydrocarbons was carried out using a double bed catalyst composed of 0.25 wt % Pd/Nb$_2$O$_5$ and Ni—Mo/ZrO$_2$. The 0.25 wt % Pd/Nb$_2$O$_5$ catalyst was prepared by loading Pd(NO$_3$)$_2$ (10 wt % Aldrich) onto niobic acid by an incipient wetness method, drying the loaded material at 393 K for 3 hours and calcining the dried material at 533 K for 3 hours in an air atmosphere. The Ni—Mo/ZrO$_2$ catalyst was prepared by loading about 10 wt % of molybdenum and about 3 wt % of Ni onto a ZrO$_2$ support. The Mo precursor used in the preparation of the catalyst was ammonium heptamolybdate tetrahydrate (hereinafter "AHM"), and the Ni precursor was nickel nitrate hexahydrate (hereinafter "NNH").

Specifically, an aqueous solution of AHM in distilled water was impregnated into a ZrO$_2$ support, dried at 423 K for 2 hours, and then continuously calcined at 732 K for 2 hours, thereby preparing Mo/ZrO$_2$. Then, NNH was dissolved in distilled water, impregnated with the Mo/ZrO$_2$ catalyst, dried at 423 K for 2 hours, and then continuously calcined at 732 K for 2 hours, thereby preparing a Ni—Mo/ZrO$_2$ catalyst.

The reaction was carried out using a high-pressure micro-reactor, and the experiment was carried out using the two catalysts, prepared as described above, in amounts of 3 g respectively (total amounts of the two catalysts are 6 g). The reduction of the catalysts was performed by heating them to 723 K at a rate of 0.5° C./min at a hydrogen flow rate of 200 sccm, maintaining them at that temperature and then lowering the temperature to 623 K. At 623 K, the ketone mixture was introduced at a WHSV of 0.5 h$^{-1}$ while the pressure of hydrogen was adjusted to 50 bar. The conversion and product selectivity of the reactants were analyzed by GC-Mass spectrometry, and the results of the analysis are shown in Table 8.

TABLE 8

| | Temperature (° C.) | | |
|---|---|---|---|
| | 250 | 300 | 350 |
| | Conversion (%) | | |
| | 98.5 | 99.7 | 100 |
| Selectivity (%) | | | |
| Branched Ketone (C5-C13) | 1.5 | 1.5 | 0.0 |
| Paraffin (C3~C4) | 0.6 | 1.3 | 1.5 |
| Paraffin (C5~C12) | 77.1 | 74.7 | 68.6 |
| Paraffin (C13~C36) | 8.5 | 14.9 | 0.5 |
| Olefin | 0.0 | 0.6 | 1.2 |
| Aromatic | 3.4 | 2.3 | 21.5 |
| Alcohol | 6.3 | 0.0 | 0.0 |
| Acid | 0.0 | 0.0 | 0.0 |
| Ether | 0.0 | 0.0 | 0.5 |
| Unknown | 2.7 | 4.7 | 6.2 |

Example 5

For the ketone mixture having the composition shown in Table 1, an experiment of preparing branched paraffinic hydrocarbons was carried out using 6 g of a catalyst by physically mixing 3 g of 0.25 wt % Pd/Nb$_2$O$_5$ and 3 g of Ni—Mo/ZrO$_2$. The 0.25 wt % Pd/Nb2O5 and Ni—Mo/ZrO2 catalysts were prepared in the same manner as described in Example 4. The reduction of the catalyst and the reaction were carried out in the same manner as Example 4, and the conversion and product selectivity of the reactants are shown in Table 9 below.

TABLE 9

| | Temperature (° C.) | | |
|---|---|---|---|
| | 250 | 300 | 350 |
| | Conversion (%) | | |
| | 97.7 | 100 | 100 |
| Selectivity (%) | | | |
| Branched Ketone (C5-C13) | 10.0 | 1.8 | 0.0 |
| Paraffin (C3~C4) | 2.4 | 0.4 | 1.4 |
| Paraffin (C5~C12) | 69.5 | 84.2 | 54.2 |
| Paraffin (C13~C36) | 2.1 | 0.0 | 0.0 |
| Olefin | 0.0 | 0.4 | 0.9 |
| Aromatic | 11.4 | 5.9 | 39.1 |
| Alcohol | 1.2 | 0.0 | 0.7 |
| Acid | 0.2 | 0.0 | 0.0 |
| Ether | 0.0 | 0.2 | 0.0 |
| Unknown | 3.1 | 7.1 | 3.7 |

Example 6

For the ketone mixture having the composition shown in Table 1, an experiment of preparing branched paraffinic hydrocarbons was carried out using a double bed catalyst composed of 0.25 wt % Pd/CeZrOx and Ni—Mo/ZrO$_2$. To prepare the 0.25 wt % Pd/CeZrOx, the CeZrOx support was prepared in the following manner. Ce(No$_3$)$_3$ 6H$_2$O and ZrO (NO$_3$)$_2$ were mixed at a ratio of 1:1 and co-precipitated for 65 hours while keeping the pH at 10 with NH$_4$OH. The precipitate was filtered, washed, dried at 383 K for a sufficient time, and then calcined at 723 K for 2 hours. The reaction was carried out using a high-pressure micro-reactor, and the experiment was carried out using the two catalysts, prepared as described above, in total amount of 6 g (3 g for each catalyst). The reduction of the catalyst and the reaction were carried out in the same manner as Example 4, and the conversion and product selectivity of the reactants are shown in Table 10 below.

TABLE 10

| | Temperature (° C.) | | |
|---|---|---|---|
| | 250 | 300 | 350 |
| | Conversion (%) | | |
| | 99.8 | 100 | 100 |
| Selectivity (%) | | | |
| Branched Ketone (C5-C13) | 1.0 | 0.7 | 0.1 |
| Paraffin (C3~C4) | 3.0 | 1.2 | 0.5 |
| Paraffin (C5~C12) | 84.0 | 72.3 | 72.0 |
| Paraffin (C13~C36) | 6.1 | 19.7 | 22.7 |
| Olefin | 0.0 | 0.2 | 0.0 |
| Aromatic | 0.0 | 0.0 | 0.0 |
| Alcohol | 4.7 | 1.8 | 1.1 |
| Acid | 0.0 | 0.0 | 0.0 |
| Ether | 0.0 | 0.2 | 0.3 |
| Unknown | 1.3 | 3.9 | 3.3 |

Example 7

For the ketone mixture having the composition shown in Table 1, an experiment of preparing branched paraffinic hydrocarbons was carried out using 6 g of a catalyst prepared by physically mixing 3 g of 0.25 wt % Pd/CeZrOx and 3 g of Ni—Mo/ZrO$_2$. The 0.25 wt % Pd/CeZrOx and Ni—Mo/ZrO$_2$ catalysts were prepared in the same manner as described in Example 6. The reduction of the catalyst and the reaction were carried out in the same manner as Example 4, and the conversion and product selectivity of the reactants are shown in Table 11 below.

TABLE 11

| | Temperature (° C.) | | |
|---|---|---|---|
| | 250 | 300 | 350 |
| | Conversion (%) | | |
| | 99 | 98 | 99.4 |
| Selectivity (%) | | | |
| Branched Ketone (C5-C13) | 2.3 | 2.6 | 1.1 |
| Paraffin (C3~C4) | 1.7 | 2.1 | 2.9 |
| Paraffin (C5~C12) | 59.1 | 88.9 | 89.2 |
| Paraffin (C13~C36) | 1.2 | 5.8 | 4.9 |
| Olefin | 0.0 | 0.0 | 0.2 |
| Aromatic | 0.1 | 0.4 | 1.3 |
| Alcohol | 34.0 | 0.0 | 0.3 |
| Acid | 0.0 | 0.0 | 0.0 |
| Ether | 0.0 | 0.0 | 0.2 |
| Unknown | 1.5 | 0.2 | 0.0 |

The invention claimed is:

1. A method of preparing paraffins for transportation fuel or lubricating base oil using biomass, the method comprising the steps of:
   A) preparing C2-C7 volatile fatty acids or their salts by fermentation of biomass;
   B) producing a mixture of C3-C13 ketones from the volatile fatty acids or their salts of step A); and
   C) converting the ketone mixture of step B) into paraffins in the presence of a hydrogenation catalyst
   wherein step C) comprises the steps of
      i) subjecting the ketone mixture to aldol condensation to prepare hydroxyketones having an increased carbon chain length;
      ii) dehydrating the hydroxyketones to form enones;
      iii) saturating the enones with hydrogen to form ketones; and
      iv) converting the formed ketones into paraffins by hydrodeoxygenation,
   and
   wherein step C) is carried out in a single reactor.

2. The method of claim 1, wherein the method further comprises, between steps ii) and iii), the steps of:
   iii-a) reacting the enones with a ketone to form hydroxyenones having an increased carbon chain length; and
   iii-b) dehydrating the hydroxyenones.

3. The method of claim 1, wherein the method further comprises, between steps ii) and iii), the steps of:
   iii-c) saturating the enones with hydrogen;
   iii-d) subjecting the ketone mixture to aldol condensation to prepare hydroxyketones having an increased carbon chain length;
   iii-e) dehydrating the hydroxyketones to form enones having an increased carbon chain length; and
   iii-f) saturating the enones of step iii-e) with hydrogen.

4. The method of claim 1, wherein the paraffins are C6-C60 branched paraffins.

5. The method of claim 1, wherein hydrogen which is used in one or more of steps B) to C) is produced in step A).

6. The method of claim 1, wherein the catalyst that is used in step C) has one or more of aldol condensation, hydrogenation and hydrodeoxygenation functions.

7. The method of claim 6, wherein the catalyst is a catalyst system obtained by physical mixing or molding using a binder.

8. The method of claim 6, wherein the catalyst is a catalyst system having a double bed structure of different catalysts.

9. The method of claim 6, wherein the catalyst has the aldol condensation function and comprises an acid or base functionality.

10. The method of claim 9, wherein the catalyst having the aldol condensation function is selected from the group consisting of CeZrOx, CuZrOx, hydrotalcite, niobium oxide, alumina, silica, silica-alumina, zirconia, titania, or mixed oxides thereof, and molecular sieves including zeolite.

11. The method of claim 6, wherein the catalyst having the hydrogenation function is a metal component selected from the group consisting of Group VIII metals, Group VI metals, and mixtures thereof, which have a hydrogenation function.

12. The method of claim 11, wherein the metal component is selected from the group consisting of Pd, Pt, Rh, Ru, Ni, Cu, V, Fe, Co, Mo, W, NiMo, CoMo, NiW, or CoW.

13. The method of claim 6, wherein the catalyst having the hydrodeoxygenation function comprises both hydrogenation and deoxygenation functions.

14. The method of claim 13, wherein the catalyst having the hydrodeoxygenation is prepared by loading the metal component having the hydrogenation function on a material comprising an acid or base functionality.

15. The method of claim 6, wherein step C) is carried out at a temperature of 80 to 500° C. at a hydrogen pressure of 1-200 bar.

16. The method of claim 1, wherein weight hourly space velocity in the single reactor is adjusted to 0 to 5/hr.

17. The method of claim 16, wherein the weight hourly space velocity is adjusted to 0 to 2/hr.

* * * * *